United States Patent [19]
Kroll

[11] Patent Number: 5,658,319
[45] Date of Patent: Aug. 19, 1997

[54] IMPLANTABLE CARDIOVERTER DEFIBRILLATOR HAVING A HIGH VOLTAGE CAPACITOR

[75] Inventor: Mark W. Kroll, Simi Valley, Calif.

[73] Assignee: Angeion Corporation, Plymouth, Minn.

[21] Appl. No.: 645,460

[22] Filed: May 13, 1996

Related U.S. Application Data

[63] Continuation of Ser. No. 342,637, Nov. 21, 1994, Pat. No. 5,527,346, which is a continuation of Ser. No. 166,212, Dec. 13, 1993, abandoned.

[51] Int. Cl.$^6$ ................................................. A61N 1/39
[52] U.S. Cl. ........................................... 607/7; 607/5
[58] Field of Search ................................. 607/5, 7

[56] References Cited

U.S. PATENT DOCUMENTS 4,168,711  9/1979  Cannon, III et al. ............ 607/5
4,504,773  3/1985  Suzuki et al. .................... 607/5

Primary Examiner—William E. Kamm
Assistant Examiner—Kennedy J. Schaetzle
Attorney, Agent, or Firm—Brad D. Pedersen

[57] ABSTRACT

The present invention is an implantable cardioverter defibrillator (ICD) system that is electrically connected to two or more implantable discharge electrodes for implantation into a human patient for treating cardiac dysrhythmias. The ICD system has a battery system and a stepup transformer for charging a capacitive storage system in response to a cardiac dysrhythmia detected by a sensing system. A plurality of electrodes are provided which are adapted to be implanted into a human patient. A primary capacitive energy storage system is provided and is corrected to the stepup transformer for storing and delivering a high voltage output of at least 1500 volts. A stepdown transformer is also provided which is connected between the primary capacitive energy storage system and the electrodes for reducing the high voltage output of the primary capacitive energy system to a safe level for the heart.

12 Claims, 3 Drawing Sheets

IMPLANTABLE CARDIOVERTER DEFIBRILLATOR HAVING A HIGH VOLTAGE CAPACITOR

RELATED APPLICATIONS

The present application is related to U.S. Pat. No. 5,391,186; the present application is a continuation of U.S. patent application Ser. No. 08/342,637 entitled "IMPLANTABLE CARDIOVERTER DEFIBRILLATOR EMPLOYING POLYMER THIN FILM CAPACITORS", filed Nov. 21, 1994, now U.S. Pat. No. 5,527,346, which is a continuation of Ser. No. 08/166,212, filed Dec. 13, 1993, now abandoned; and is related to U.S. patent application Ser. No. 08/645,199 entitled "CAPACITIVE SWITCHING OUTPUT FOR IMPLANTABLE CARDIOVERTER DEFIBRILLATORS" which are assigned to the Assignee of the present invention and the disclosures of which are herein incorporated by referenced.

FIELD OF THE INVENTION

The present invention relates generally to implantable cardioverter defibrillators and in particular, to an implantable cardioverter defibrillator utilizing a high voltage capacitor.

BACKGROUND OF THE INVENTION

Implantable cardiac defibrillator (ICD) systems are commonly used today to prevent sudden cardiac deaths. The primary components of all existing ICD systems include an automatic monitoring and detection mechanism, a capacitor system, a battery system and control circuitry for detecting a ventricular arrythmia and controlling delivery of a high voltage capacitive discharge electrical countershock in response to the detected arrythmia by charging and then discharging the capacitor system. To achieve successful defibrillation, the ICD system must deliver a high voltage electrical countershock with an initial voltage of greater than about 500 to 600 volts.

Most existing ICD systems are capable of delivering a maximum countershock of up to 700 to 750 volts having a total energy of between 31 to 44 joules. The capacitor system is a critical element of the ICD system, both in terms of how effective the ICD system is and how small the ICD system is. The capacitor component is the largest single component in the ICD. By definition, a capacitor is comprised of two conductive surfaces separated by an insulating material. The insulating material is known as the "dielectric" of the capacitor. When the two surfaces of the capacitor are oppositely charged by a voltage source, such as the battery in an ICD system, electrical energy is effectively stored by the capacitor in the polarized dielectric. The capability of the capacitor to store an electrical charge is the capacitance value of capacitor. For a given dielectric material, the thinner the dielectric, the higher the capacitance value. A thinner dielectric also decreases the overall size of the capacitor. Unfortunately, there are limits as to how thin a dielectric can be due to the fact that very thin dielectrics will break down under high voltages as there is simply an insufficient amount of insulation material between the conductive surfaces to withstand the high voltages.

When all of the requirements for an ICD system are considered, the aluminum oxide electrolytic capacitor (also known as a photo flash capacitor) has proven to be the best capacitor technology for use in ICD systems to date. The aluminum oxide dielectric can be made very thin because the dielectric oxide is essentially grown on the conductive surfaces of a very thin sheet of aluminum that has been etched to increase its effective surface area. As a result, aluminum oxide electrolytic capacitors have higher energy densities (typically 1.7 to 1.8 joules per cc) than other types of capacitor technologies (typically much less than 1.5 joules per cc). Due to the nature of the aluminum oxide dielectric, electrolytic capacitors are typically limited to a maximum rated charging voltage in the range of approximately 350 to 375 volts. Beyond 375 volts, electrolytic capacitors begin to suffer from significant leakage current across the dielectric. This leakage current increases rapidly as the voltage is increased and charging of the electrolytic capacitor will cease when the leakage current equals the charge current. As a result, most existing ICD systems utilize two electrolytic capacitors in series, each being charged with approximately 375 volts, which are then discharged to deliver the high voltage shock to the myocardium having a maximum voltage of approximately 750 volts.

Although electrolytic capacitors are used in most existing ICD systems in order to take advantage of their excellent capacitance to volume ratio, electrolytic capacitors suffer from several major drawbacks. First, as stated above, the useful charging voltage for electrolytic capacitors is limited to approximately 375 volts due to the leakage current encountered at higher charging voltages. This requires that two electrolytic capacitors be used which increases the number of components within the ICD system.

Another significant disadvantage of electrolytic capacitors is the degradation of the oxide dielectric over time. Although the dielectric degrades, it can be reformed by periodic charging to full voltage. On a monthly or quarterly basis, the capacitor system will need to be charged to its full voltage. In early ICD systems, this requirement necessitated the patient's periodic return to the hospital to accomplish the reforming of the capacitor system. Later ICD systems have used automatic reforming of the electrolytic capacitors from the internal battery system on a periodic basis. This practice is wasteful of valuable energy in ICD system that only has a finite and depletable source of power.

Still another drawback of the electrolytic capacitors is that a substantial portion of the energy density advantage over other capacitive technology is lost to packaging inefficiencies within the ICD system as a result of the cylindrical packaging shape that is required of electrolytic capacitors. When the lost volume of fitting a cylindrical volume into a rectangular volume is factored into the energy density calculations, the energy density for electrolytic capacitors is effectively only about 1.3 to 1.4 joules per cc.

The highest density energy storage capacitors available are high voltage thin film capacitors which are capable of densities on the order of four joules per cc. In thin film capacitors, the dielectric is a very thin polymer film that is formed mechanically through high precision rolling operations. Conductive layers of aluminum are then deposited on each surface for the polymer film. One advantage of thin film capacitors are that they have very high breakdown voltages and very good charge retention. As a result, if a polymer thin film capacitor were used in an ICD system, there would be no need to use two separate capacitors to achieve the initial discharge voltage required for defibrillation. Nor would there be any need to reform the capacitor due to breakdown of the dielectric. They are also manufacturable in almost any shape.

Unfortunately, to achieve densities in the range of four joules per cc, the thin film must be charged up to high voltages on the order of 2000 volts or greater. The highest densities do not occur until around 4000 volts. Unfortunately, these voltages would damage the heart. For instance, myocardial tissue resistance between any two implanted discharge electrodes has been found to be about 50 ohms on average. Using this average resistance value, the peak current of an electrical countershock delivered from a capacitor charged to 2000 volts would be 40 amps. It is known that peak currents in excess of about 30 amps during delivery of an electrical countershock can lead to tissue destruction in the heart in a zone beginning from the center of the electrical field and extending outward. High peak currents also stun tissue extending radially outward from the border of the destruction zone for some additional distance.

Another problem with discharge voltages of 2000 volts or greater, for a given level of energy storage is that the capacitor size would be such that the pulse width would be inefficient. For example, to store 25 joules in a film capacitor of 2100 volts would require a capacitance of 11.3 microfarads. Such a capacitor would have a time constant of about 0.5 milliseconds when delivering a charge to a 50 ohm heart load. Such a pulse width is significantly shorter than the optimal duration for defibrillation which is on the order of two to five milliseconds.

One approach to using thin film capacitors in an ICD is taught in U.S. Ser. No. 08/342,637 filed Nov. 21, 1994 which is a continuation of 08/166,212, filed Dec. 13, 1993 entitled IMPLANTABLE CARDIOVERTER DEFIBRILLATOR EMPLOYING POLYMER THIN FILM CAPACITORS, which is assigned to the assignee of the present application and the disclosure of which is herein incorporated by reference. This application has the drawback that the body or the heart may be exposed to the full voltage from the primary film capacitor even though the average voltage is moderate due to chopping.

Another possible approach for film capacitors is taught in U.S. Pat. No. 5,391,186 entitled METHOD AND APPARATUS FOR UTILIZING SHORT TAU CAPACITORS IN AN ICD, which is assigned to the assignee of the present invention and which is herein incorporated by reference. Once again, this system allows the body or the heart to be exposed to the full voltage of primary film capacitor even though the average voltage is moderated due to chopping.

While the use of electrolytic capacitors for ICD systems has allowed for the creation of practical implantable devices that can deliver effective electrical countershocks, there are inherent limitations of the electrolytic capacitors which hinder further reduction in the size of ICD systems by reducing the size of the capacitor systems necessary to deliver the capacitive discharge electrical countershock. Therefore, it is desirable to provide an implantable cardioverter defibrillator system which could employ the use of capacitor technology other than the electrolytic capacitors. In addition, it would be advantageous to provide an implantable cardioverter defibrillator system that could take advantage of the higher charging voltages available with thin film capacitors while protecting the body or heart from being exposed to the full voltage of these higher charging voltage capacitors.

SUMMARY OF THE INVENTION

The present invention is an implantable cardioverter defibrillator (ICD) system that is electrically connected to two or more implantable discharge electrodes for implantation into a human patient for treating cardiac dysrhythmias. The ICD system has a battery system and a stepup transformer for charging a capacitive storage system in response to a cardiac dysrhythmia detected by a sensing system. A plurality of electrodes are provided which are adapted to be implanted into a human patient. A primary capacitive energy storage system is provided and is connected to the stepup transformer for storing and delivering a high voltage output of at least 1500 volts. A stepdown transformer is also provided which is connected between the primary capacitive energy storage system and the electrodes for reducing the high voltage output of the primary capacitive energy system to a safe level for delivery to the heart.

DETAILED DESCRIPTION OF THE DRAWINGS

Figure 1:
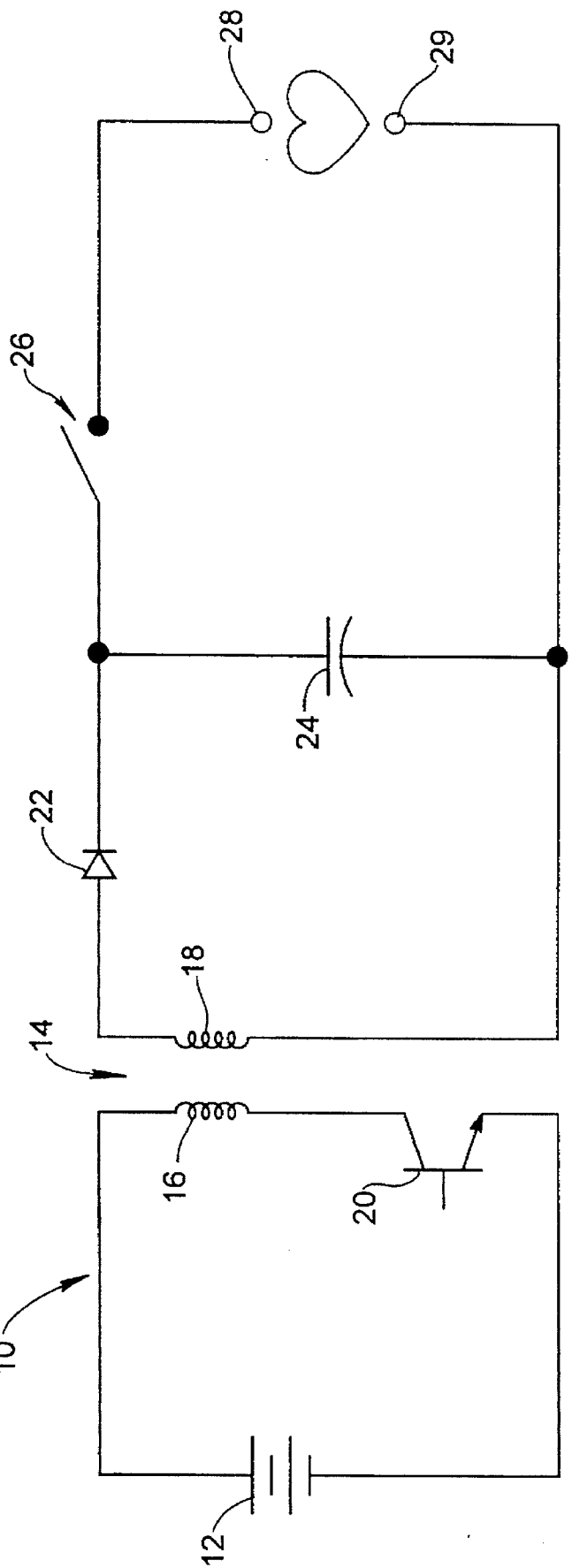
FIG. 1 is a simplified circuit diagram of a prior art implantable defibrillator circuit.

FIG. 1 is a simplified circuit diagram of a known implantable defibrillator circuit 10. Circuit 10 comprises a high current defibrillation battery 12, which is typically a lithium silver vanadium pentoxide ($LiAgVO_5$) battery, however, many other types of batteries may be used such as lithium titanium disulfide ($LiTiS_2$) without departing from the spirit or scope of the invention. A high voltage stepup transformer 14 is provided which comprises a primary coil 16 and a secondary coil 18. A transistor switch 20 is provided to drive primary coil 16. Transistor switch 20 provides an alternating current through primary coil 16 of transformer 14. Secondary coil 18 produces a significantly higher voltage which is rectified by a diode 22 and stored in a storage capacitor 24. A semiconductor switch 26 is connected to storage capacitor 24. Electrodes 28 and 29 are connected to switch 26 and are positioned adjacent a patient's heart. When capacitor 24 is fully charged, switch 26 is activated to complete the circuit which delivers the charge of capacitor 24 to electrodes 28, 29 for defibrillation of the heart.

Figure 2:
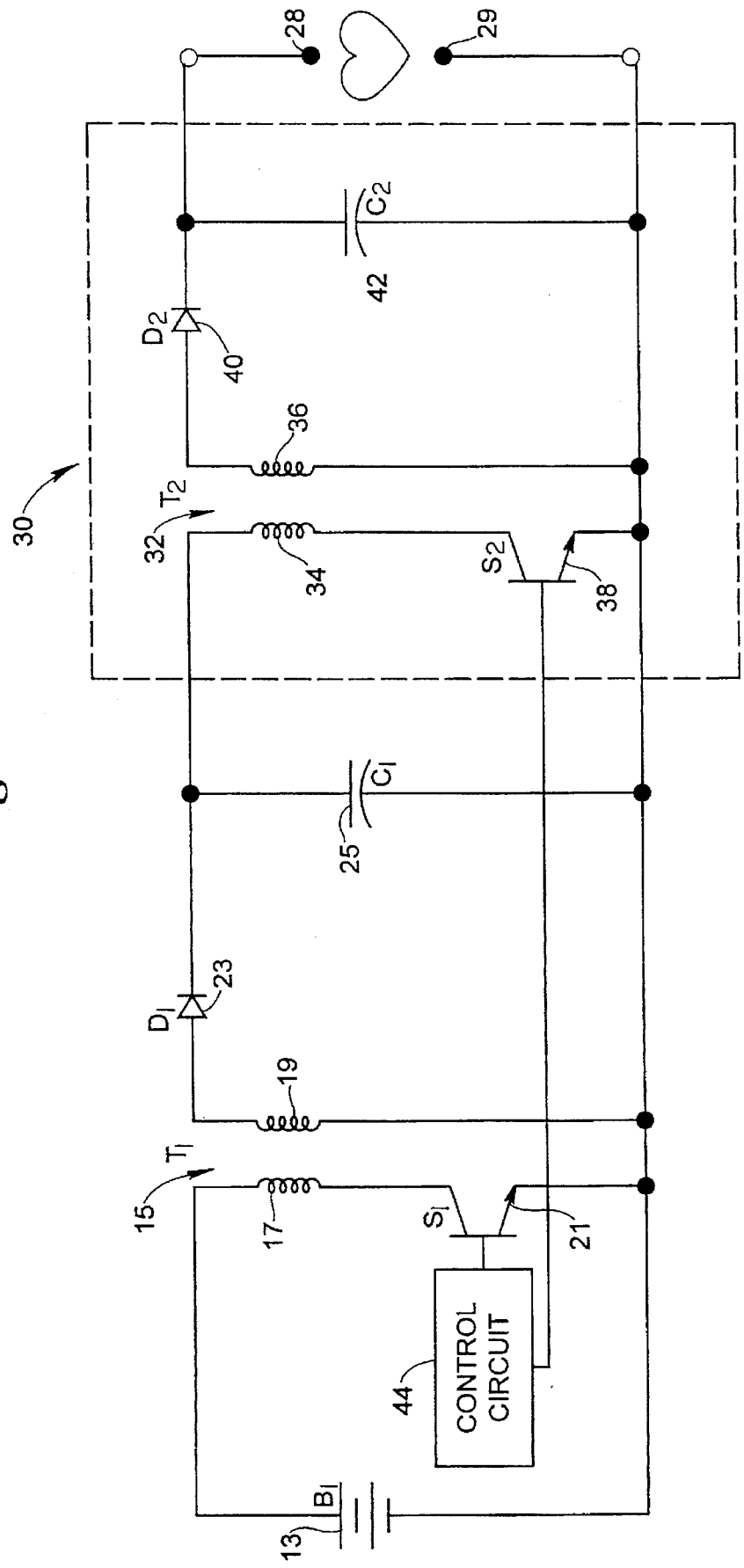
FIG. 2 is a simplified circuit diagram of the present invention.

FIG. 2 illustrates a simplified circuit diagram of the present invention. The present invention has a high current defibrillation battery 13 which as described above with reference to FIG. 1, is typically a lithium silver vanadium pentoxide ($LiAgVO_5$) battery. A high voltage setup transformer 15 is provided which comprises a primary coil 17 and secondary coil 19. A transistor switch 21 is provided to drive primary coil 17. Secondary coil 19 produces a significantly higher voltage that is rectified by a diode 23 and stored in a storage capacitor 25. In the present invention, storage capacitor 25 is preferably a 2000 volt polyester film capacitor. Other capacitors having voltages from 1500 volts or higher could also be used as well as capacitors having other dielectric materials besides polyester without departing from the spirit or scope of the present invention.

As in FIG. 1, electrodes 28 and 29 are provided adjacent a patient's heart. Connected between capacitor 25 and electrodes 28 and 29 is a stepdown transformer circuit 30 outlined by a dashed line. Stepdown transformer circuit 30 comprises a step down transformer 32 having a primary coil 34 and a secondary coil 36. Transistor switch 38 is provided to drive primary coil 34. As with transistor switch 21, transistor switch 38 provides an alternating curve through primary coil 34 of transformer 32. A rectifying diode 40 is provided connected to secondary coil 36 and a small filter capacitor 42 is provided for smoothing the signal from secondary coil 36. A control circuit 44 is also provided to control the operation of transistor switches 21 and 38. For ease of understanding the present invention, the control circuit is being illustrated only schematically at block 44.

In operation, when it is decided that a shock should be delivered to electrodes 28 and 29 by a sensing system (not shown), capacitor 25 must be charged. The charging of capacitor 25 takes place over a period of approximately 5 seconds. To charge capacitor 25, control circuit 44 pulses switch 21 on and off to provide an alternating current through primary coil 17 of transformer 15. The output from transformer 18 is steered through diode 23 and stored in capacitor 25. When capacitor 25 is fully charged, or if capacitor 25 was already charged, the voltage from capacitor 25 is used to drive a current through primary coil 34 of transformer 32. This is done through the operation of switch 38 which is controlled by control circuit 44. The stepped down voltage at coil 36 is then steered through diode 40 and is smoothed by capacitor 42 for delivery to electrodes 28 and 29.

It is important that the voltage from capacitor 25 be stepped down to prevent damage to the heart. As stated in the background section, myocardial tissue is between any two implanted discharge electrodes has been found to be approximately 50 ohms on average. Using this average resistance value, the peak current of an electrical countershock delivered from capacitor charged to 2000 volts would be 40 amps. It is known that peak currents in excess of about 30 amps during delivery of an alternate countershock can lead to tissue destruction in the heart its own beginning from the central of the electrical field and extending outward. High peak currents also stun tissue extending radially outward from the border of destruction zone for some additional distance. Thus by utilizing the present invention, damage to the patient's heart may be eliminated by stepping down the voltage. In the preferred embodiment of the present invention, the peak current of a countershock applied to a patient's heart via electrodes 28 and 29 from coil 36 is 20 amps. This is well below the value where damage will be done to the heart.

Figure 3:
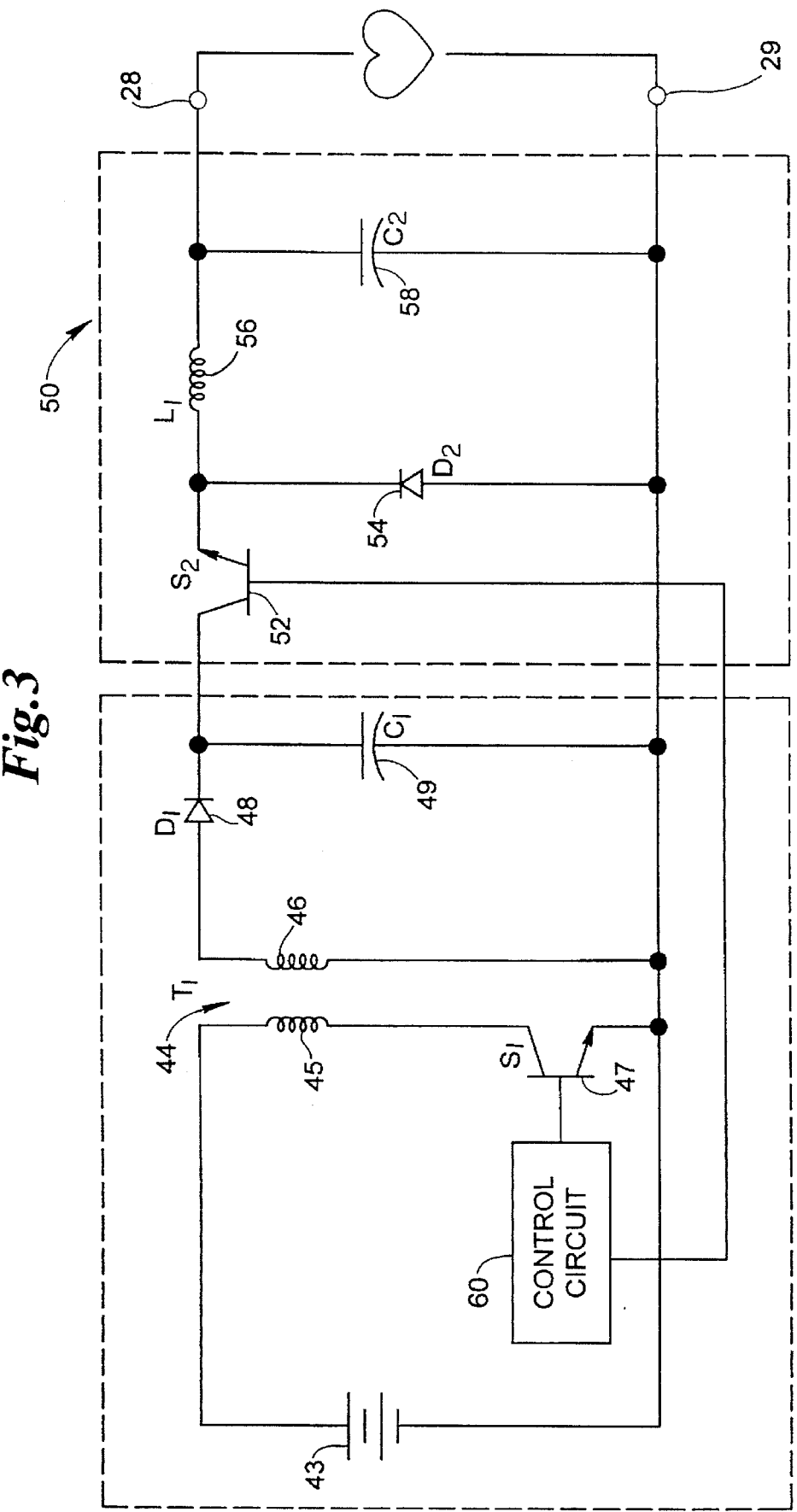
FIG. 3 is an alternative embodiment of the present invention.

FIG. 3 is an alternative embodiment of the present invention. The alternative embodiment has a high current defibrillator battery 43, which is preferably a $LiAgVO_5$ battery. A high voltage transformer 44 is provided which comprises a primary coil 45 and a secondary coil 46. A transceiver switch 47 is provided to control operation of transformer 44. Secondary coil 46 produces a significantly higher voltage that is rectified by a diode 48 and stored in a capacitor 49. Capacitor 49 is once again a high voltage capacitor, typically a 2000 volt polyester film capacitor. In this embodiment, instead of a stepddown transformer circuit 30 as in FIG. 2, the alternative embodiment has a buck converter 50 connected between capacitor 49 and electrodes 28 and 29. Buck converter 50 includes a transistor switch 52, a diode 54, an inductor 56 and a small filtering capacitor 58. As in FIG. 2, a control circuit 60 is shown schematically for controlling the operation of transistor switches 47 and 52.

In operation, capacitor 49 is charged as in FIG. 2. When it is determined that a countershock is to be applied to electrodes 28, 29, switch 52 is turned on by control circuit 60. The voltage from capacitor 49 is applied across inductor 56 because of the low resistance of the patient's heart. The current through inductor 56 quickly increases according to the rule I=V x (the integral of the voltage). When the current in the inductor reaches the saturation level of the inductor, switch 52 is turned off. The voltage across inductor 56 then responds to the basic equation for inductors which is V=L (di/dt), which means that the voltage now changes polarity since the current has gone to zero. This reverse polarity allows diode 54 to continue to force current through the heart.

What is claimed is:

1. An implantable cardioverter defibrillator apparatus for treating cardiac dysrhythmias including a battery system and a stepup transformer for charging a storage device in response to a cardiac dysrhythmia detected by a sensing system, the apparatus comprising:

a plurality of implantable sensing and discharge electrodes adapted to be located in a human patient;

a primary capacitive energy storage system connected to the stepup transformer for storing and delivering a high voltage output of at least 1500 volts; and a stepdown transformer connected between the primary capacitive energy storage system and the electrodes for reducing the high voltage out-put of the primary capacitive energy storage system to desired output pulse level.

2. The apparatus as in claim 1 further comprising a control system connected to the stepdown transformer and to the primary capacitive energy storage system for controlling the charging of the primary capacitive energy storage system and for controlling the stepdown transformer.

3. The apparatus as in claim 1 wherein the desired output pulse level is below 20 amps.

4. The apparatus as in claim 1 wherein the primary capacitive energy storage system has a thin film capacitor.

5. The apparatus as in claim 4, wherein the thin film capacitor is a polyester thin film capacitor.

6. The apparatus as in claim 1 further comprising a filter capacitor between the step down transformer and the electrodes.

7. An implantable cardioverter defibrillator apparatus for treating cardiac dysrhythmias including a battery system and a stepup transformer for charging a storage device in response to a cardiac dysrhythmia detected by a sensing system, the apparatus comprising:

a plurality of implantable sensing and discharge electrodes adapted to be located in a human patient;

a primary capacitive energy storage system connected to the stepup transformer for storing and delivering a high voltage output of at least 1500 volts; and a current limiting circuit connected between the primary capacitive energy storage system and the electrodes wherein the current limiting circuit has a limiting switch and an inductor for limiting the current to the electrodes to a desired level.

8. The apparatus as in claim 7 further comprising a control system connected to the current limiting circuit and to the primary capacitive energy storage system for controlling the charging of the primary capacitive energy storage system and for controlling the current limiting circuit.

9. The apparatus as in claim 7 wherein desired level of current to the electrodes is below 20 amps.

10. The apparatus as in claim 7 wherein the primary capacitive energy storage system has a thin film capacitor.

11. The apparatus as in claim 7, wherein the thin film capacitor is a polyester thin film capacitor.

12. The apparatus as in claim 7 further comprising a filter capacitor between the current limiting circuit and the electrodes.

* * * * *